United States Patent
Pirc

(12)
(10) Patent No.: US 6,356,778 B1
(45) Date of Patent: Mar. 12, 2002

(54) CONNECTOR ASSEMBLY FOR FETAL SCALP ELECTRODE

(75) Inventor: Douglas J. Pirc, Orange, CT (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 0 days.

(21) Appl. No.: 09/521,458

(22) Filed: Mar. 8, 2000

(51) Int. Cl.$^7$ .............................................. A61B 5/0448
(52) U.S. Cl. ...................... 600/376; 600/511; 439/668; 439/675; 439/852; 439/909
(58) Field of Search .............................. 600/376, 394, 600/511; 607/37, 119, 122, 127; 439/909, 668, 675, 852

(56) References Cited

U.S. PATENT DOCUMENTS

| | | | |
|---|---|---|---|
| 3,302,159 A | * | 1/1967 | Schumacher ................ 439/675 |
| 3,827,428 A | | 8/1974 | Hon et al. |
| 3,910,271 A | | 10/1975 | Neward |
| RE28,990 E | | 10/1976 | Hon et al. |
| 5,074,809 A | * | 12/1991 | Rousseau .................... 439/675 |
| 5,168,876 A | | 12/1992 | Quedens et al. |
| 5,199,432 A | | 4/1993 | Quedens et al. |
| 5,205,288 A | | 4/1993 | Quedens et al. |
| 5,257,622 A | | 11/1993 | Hooper et al. |
| 5,324,311 A | * | 6/1994 | Acken ......................... 607/37 |
| 5,373,843 A | | 12/1994 | Quedens et al. |
| 5,377,677 A | | 1/1995 | Dowd et al. |
| 5,388,579 A | | 2/1995 | Dowd et al. |
| 5,404,876 A | | 4/1995 | DiSabito et al. |
| 5,615,674 A | | 4/1997 | Maurer |
| 5,662,103 A | | 9/1997 | Smith et al. |
| 5,665,477 A | | 9/1997 | Meathrel et al. |
| 5,671,736 A | | 9/1997 | Pettit et al. |
| 5,680,859 A | | 10/1997 | Urion et al. |

* cited by examiner

Primary Examiner—Lee Cohen
(74) Attorney, Agent, or Firm—Michael Best & Friedrich LLP

(57) ABSTRACT

A connector assembly for a fetal scalp electrode for use in monitoring fetal heart rate. The connector assembly is used in conjunction with a fetal monitor coupling device and includes a holder formed of an insulating material and a fetal electrode and a maternal electrode secured to the holder. Each wire of an insulated pair of elongated flexible wires is electrically connected to a respective one of the fetal and maternal electrodes. The connector assembly further includes a connector having a pin contact electrically connected to one of the wires and a cylindrical contact electrically connected to the other of the wires. The cylindrical contact is mounted coaxially with the pin contact so that the contacts are electrically isolated from each other and are positioned to make electrical contact with complementary contacts in the coupling device. The connector assembly also preferably includes an elongated tubular sheath that covers the connector and is sized to be received in the coupling device. The sheath has a first end extending over and receiving the ends of the pair of flexible wires, and a second end that is open and spaced from each of the contacts so that a gap is formed between the contacts and the second end of the sheath.

18 Claims, 9 Drawing Sheets

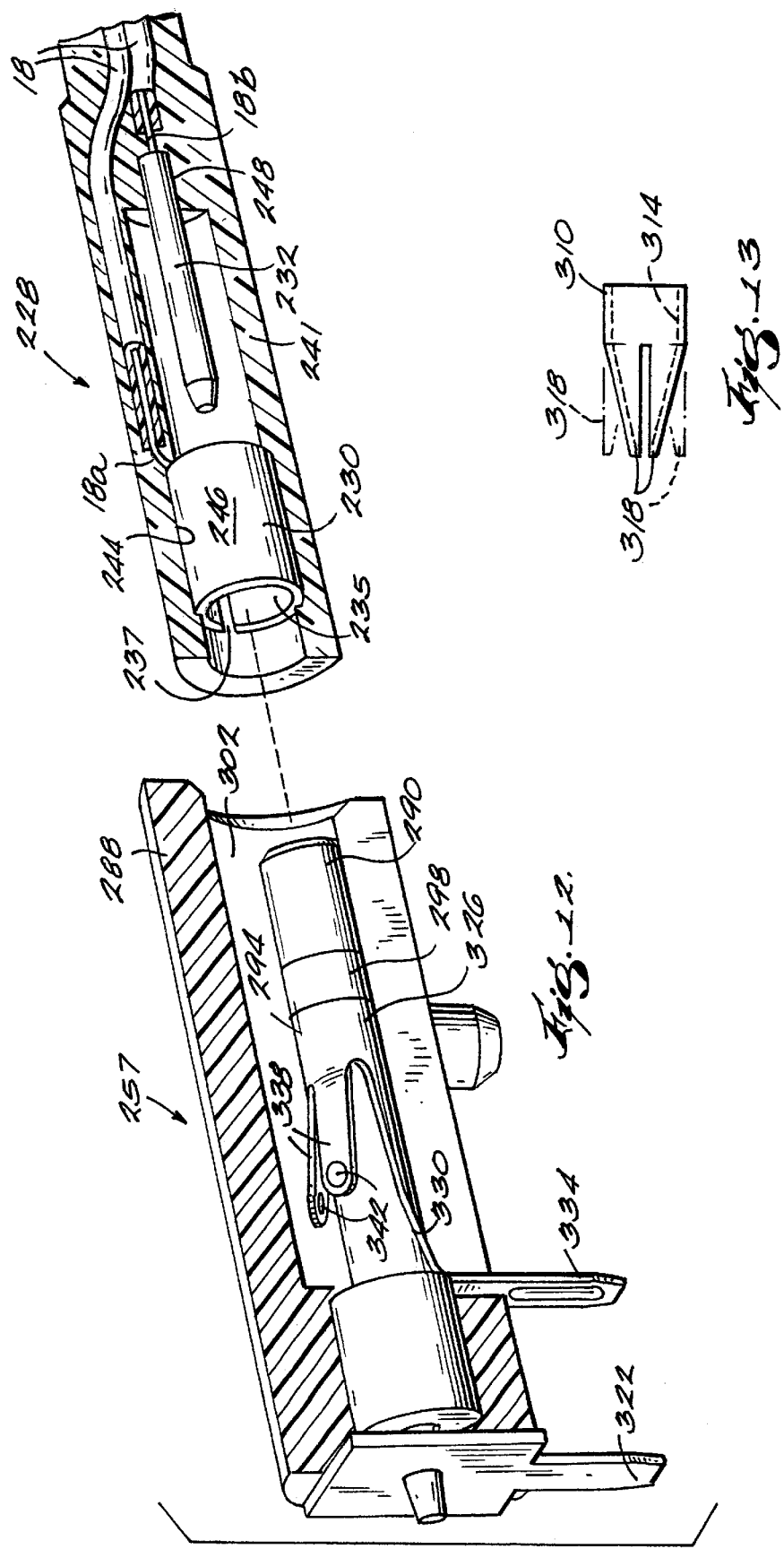

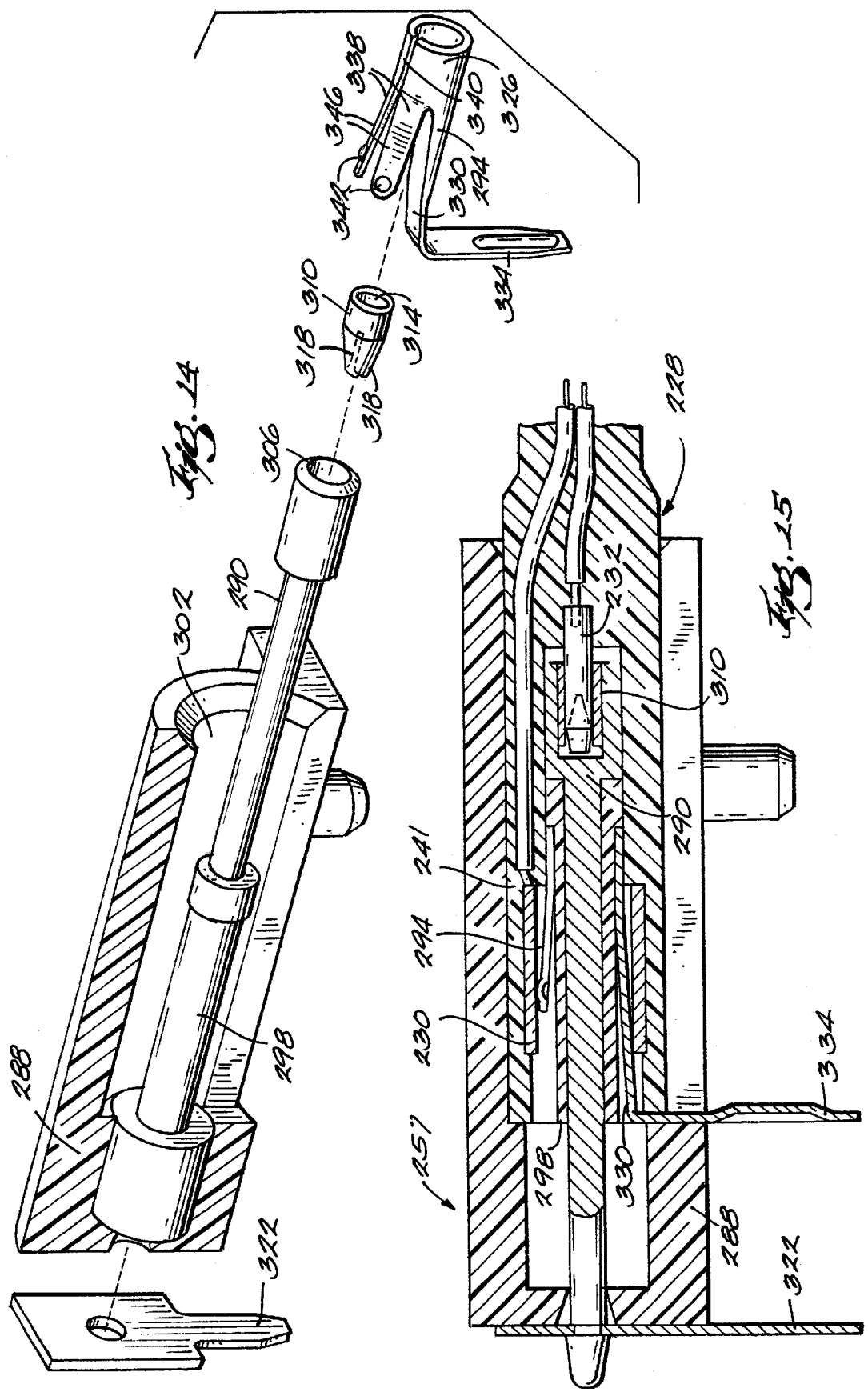

CONNECTOR ASSEMBLY FOR FETAL SCALP ELECTRODE

BACKGROUND OF THE INVENTION

This invention relates to fetal probes, and more particularly to a connector assembly for coupling a fetal electrode to a remote monitoring device.

One type of fetal probe comprises a bipolar fetal electrode commonly used to monitor fetal heart rate during birth. This type of probe consists of a spiral fetal electrode mounted on a carrier along with an electrically isolated maternal electrode. A twisted pair of wires are connected at one end to the fetal and maternal electrodes and at their opposite ends to a connector. One such connector consists of a pair of axially spaced electrodes which are electrically isolated and each of which is connected to one of the wires. The connector is adapted to be coupled to a socket having axially spaced connectors which, in turn, are coupled by a cable to the monitor.

Initially, the twisted pair of conductors and the connector are disposed in a hollow drive tube. The end of the drive tube is inserted into the mother's cervix until the forward end contacts the fetus. The role of the drive tube is to push forwardly until the spiral fetal electrode at the forward end makes contact with the fetal epidermis. The drive tube is then rotated to screw the spiral electrode into the fetal epidermis. The drive tube is then slid over the wires and the connector while the bipolar electrodes and the twisted pair of wires remain within the mother and connected to the fetus. The removal of prior art tubes required the dexterous manipulation of the drive tube which were designed to maintain a grip on the twisted pair so as to insure that the drive tube is engaged at the distal end. Defeating the grip tended to be cumbersome.

In these prior art connectors, the connector at the other end of the twisted pair of conductors is exposed. Such exposed electrodes could soil or contact energy sources and tend to be disconcerting to the patient or her partner.

In one type of assembly the socket for receiving the connector is mounted on a support or circuit board which electrically connects to a plate mounted on the mother's leg by an adhesive pad and provides a reference for the fetal and maternal electrodes. The support or circuit board connects to the leg plate by a snap electrical connector. Such snap connectors do not uniformly provide a distinct snap to indicate that good electrical contact has been achieved. In addition, the forces necessary to couple and disconnect the contacts are not consistent. As a result, medical personnel may not be aware should a good electrical connection not be achieved.

SUMMARY OF THE INVENTION

Federal Food and Drug Administration regulations now require that the connectors be designed such that no conductive connector that is remote from the patient can contact earth or any possibly hazardous voltages. One example of a connector designed for compliance with the modern regulations is disclosed in co-pending application Ser. No. 09/237,468, which is hereby incorporated herein by reference. This connector includes first and second tubular contacts axially separated and electrically isolated from each other. The tubular contacts are positioned to make electrical contact with complementary contact members in the coupling device. An elongated tubular insulating sheath covers the tubular contacts so that they are not exposed to potentially hazardous voltages.

The present invention provides another connector assembly embodiment for a fetal scalp electrode used to monitor fetal heart rate. The connector assembly is used in conjunction with a fetal monitor coupling device and includes a holder formed of an insulating material and a fetal electrode and a maternal electrode secured to the holder. Each wire of an insulated pair of elongated flexible wires is electrically connected to a respective one of the fetal and maternal electrodes. The connector assembly further includes a connector having a pin contact electrically connected to one of the wires and a cylindrical contact electrically connected to the other of the wires. The cylindrical contact is mounted coaxially with the pin contact so that the contacts are electrically isolated from each other and are positioned to make electrical contact with complementary contacts in the coupling device.

The connector assembly also preferably includes an elongated tubular sheath that covers the connector and is sized to be received in the coupling device. The sheath has a first end extending over and receiving the ends of the pair of flexible wires, and a second end that is open and spaced from each of the contacts so that a gap is formed between the contacts and the second end of the sheath.

The coupling device includes a housing defining a cavity having an opening for receiving the connector. A center conductor is mounted in the cavity and includes a tubular portion substantially coaxial with and spaced from the opening. Inside the tubular portion is an internal spring contact that includes an inwardly biased resilient spring contact finger extending away from the opening. An outer conductor is also mounted in the cavity and includes a tubular portion that is coaxial with and electrically isolated from the center conductor. The outer conductor also includes an outwardly biased resilient spring contact finger extending from the tubular portion and away from the opening.

BRIEF DESCRIPTION OF THE DRAWINGS

FIG. 12 is a cross-sectional view of yet another embodiment of a connector and a plug;

FIG. 13 is a perspective view of an internal spring contact which forms a portion of the assembly in FIG. 12;

FIG. 14 is an exploded perspective view of the plug in FIG. 12; and

FIG. 15 is a cross-sectional view of the connector and the plug in FIG. 12 shown in engaged relation.

DESCRIPTION OF THE PREFERRED EMBODIMENT

Figure 1:
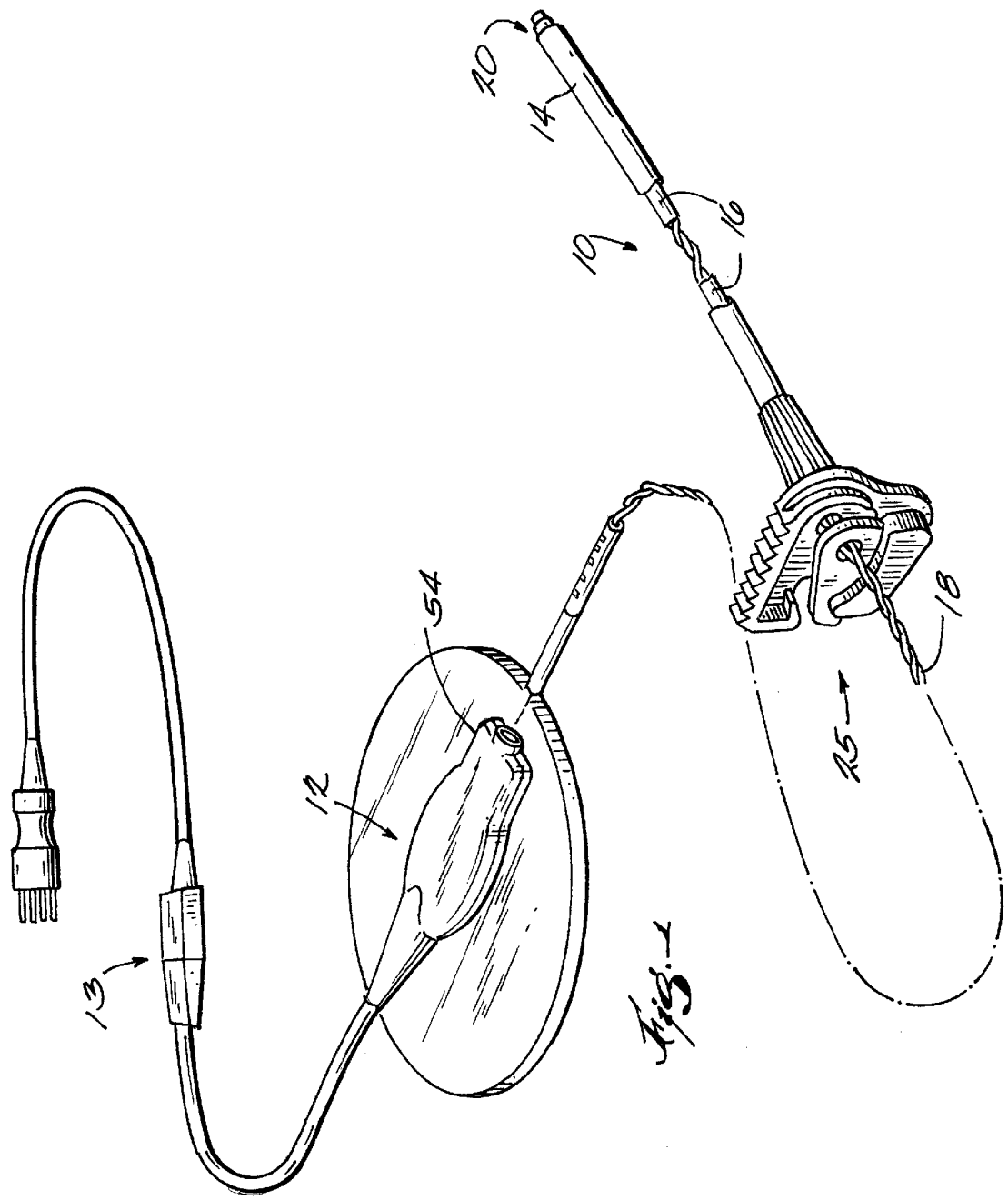
FIG. 1 is an exploded perspective view of an embodiment of a fetal electrode assembly according to the invention.

Before one embodiment of the invention is explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein is for the purpose of description and should not be regarded as limiting. The use of "including" and "comprising" and variations thereof herein is meant to encompass the items listed thereafter and equivalents thereof as well as additional items.

Figure 2:
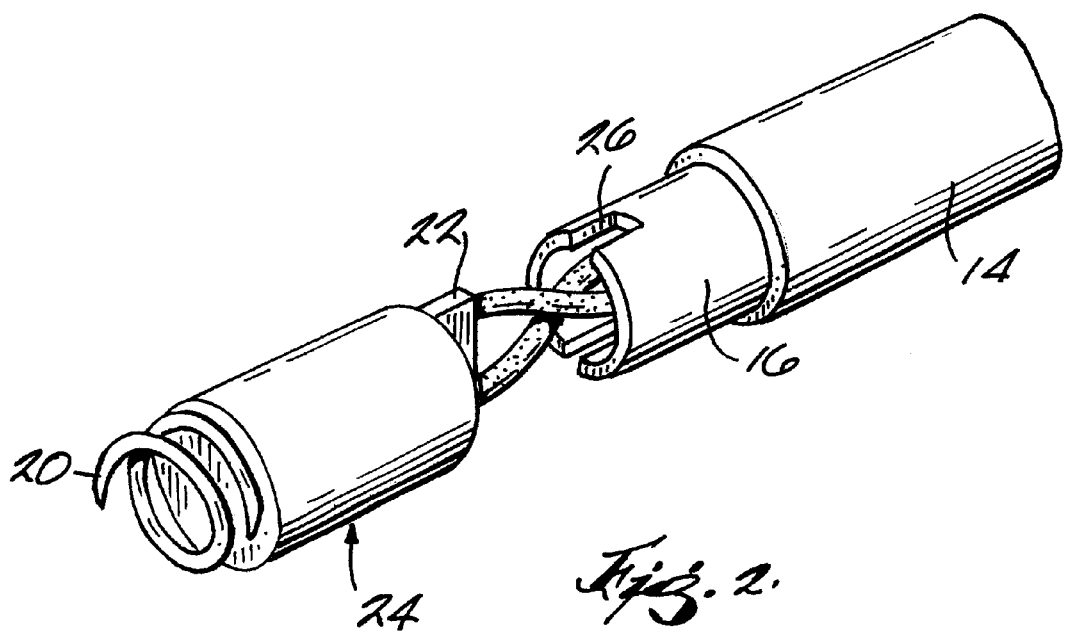
FIG. 2 is a perspective view of the forward end of a bipolar fetal electrode which forms a part of the connector assembly shown in FIG. 1.

A connector assembly for a fetal scalp electrode embodying the invention, is shown in FIGS. 1 and 2. The connector assembly includes an electrode and drive assembly 10 for coupling to a fetus and the mother, a coupling assembly 12 and a cable assembly 13 for connecting the electrode assembly to a fetal monitor (not shown).

The electrode and drive assembly 10 includes a guide tube 14, a driving tube 16, and a twisted pair of wires 18, the distal ends of which are connected, respectively, to fetal and maternal electrodes 20 and 22. A nonconductive plastic holder 24 supports and electrically insulates the fetal electrode 20 from the maternal electrode 22. The guide tube 14 has a larger diameter than and is telescopingly received over the drive tube 16. At the proximal end of the drive tube 16 there is a wire clamp 25.

The fetal electrode 20, shown in FIG. 2, is in the form of a spiral electrode having a pointed end. The maternal electrode 22 is engaged by slots 26 in the forward end of the driving tube 16 so that the pointed end of the fetal electrode 20 can be rotated and be driven into the fetal epidermis by the rotation of the driving tube 16. After the spiral electrode 20 has engaged the fetus, the guide and driving tubes 14 and 16 may be pulled over a connector 28 at the proximal end of the twisted pair 18, which remain in the birth canal. For more complete description of the fetal and maternal electrodes 20 and 22 and the holder 24, reference is made to U.S. Pat. No. Re 28,990, which is incorporated by reference herein.

Figure 3:
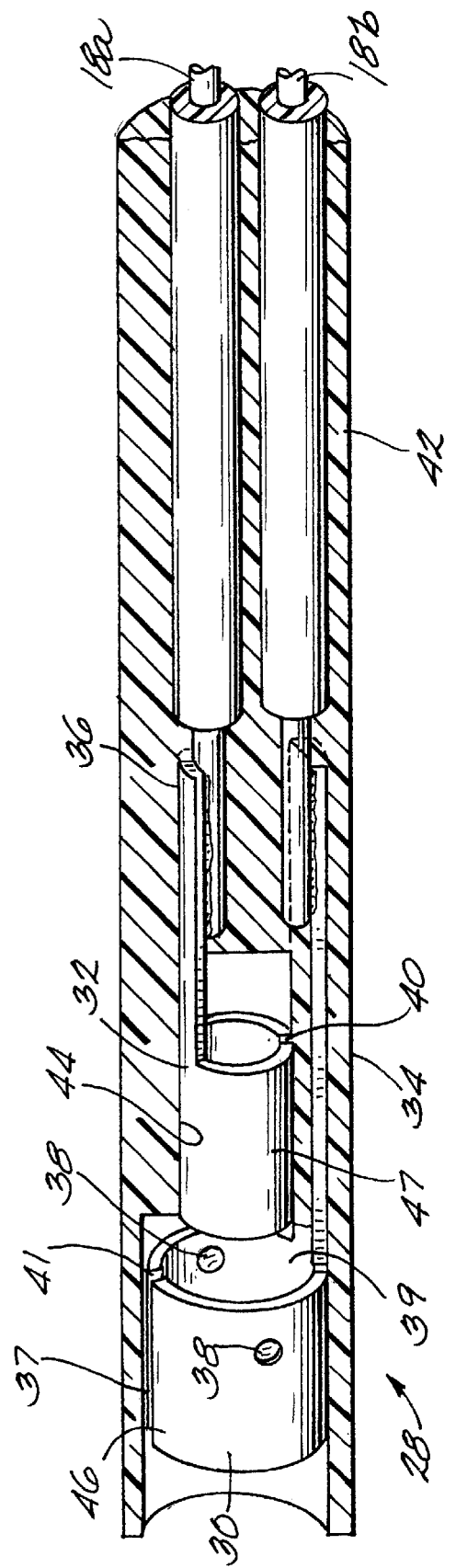
FIG. 3 is a perspective view, with parts broken away, of the connector which forms a portion of the assembly shown in FIG. 1.

FIG. 3 shows the connector 28 attached to the proximal end of the twisted pair 18 in accordance with the invention. The connector 28 comprises a generally cylindrical forward contact 30 and a coaxial rear cylindrical contact 32, each of which is formed of a suitable conductive material, such as copper, brass or nickel. Contacts 30 and 32 have an elongate, rearwardly extending tail portions 34 and 36, respectively. Each tail portion 34 and 36 has a surface for respectively receiving conductors 18a and 18b of the twisted pair 18 and to which each is connected in a suitable manner, such as by welding or soldering. The forward contact 30 has a elongate slit 37 to permit some expansion and preferably has one or more dimples 38 extending from its inner surface 39 which act as detents. A similar slit 40 is formed in the rear contact 32. A shell or sheath 41 is fixed in a surrounding relation to the contacts 30 and 32 and its rear end is overmolded at 42 to bond to the twisted pair 18. The inner surface 44 of the sheath 41 engages the outer surfaces 46 and 47, respectively, of the contacts 30 and 32 and of the tail portions 34 and 36. The forward end of the sheath 41 extends beyond the forward end of the contact 30 and a portion of the sheath 41 fills the gap between the outer surface 47 of contact 32 and the tail portion 34 of the front contact 30.

The coupling assembly 12 is shown in FIGS. 1, and 4–6 to include a housing 54, a suitable support which may take the form of a circuit board 56, a coaxial plug 57, a snap spring contact 58 and a mounting member 59. The housing 54 is preferably molded of upper and lower portions 54a and 54b which are suitably joined to enclose the circuit board 56 and the various components mounted thereon. The coupling assembly 12 cooperatively engages a conventional or specific electrode 60 adapted to be mounted, for example, on the skin of the mother. In particular, the snap spring 58 is formed of a resilient conductive metallic material and includes a pair of parallel spaced legs 61. One end of each leg 61 is free and the opposite ends are interconnected by a resilient loop 62. The legs 61 are adapted to resiliently engage the snap connector 63 of the electrode 60. The snap spring 58 also has a coupling loop 64 which is received in an opening 65 in circuit board 56 for electrically and mechanically connecting the spring 58 to the circuit board. The spring 58 performs the dual functions of securing the connector 63 and providing an electrical connection thereto.

The spring 58 is received within a recess 66 formed in the lower surface of member 59. The mounting member 59 includes a plurality of indexing legs 67 which are receivable in holes 68 in circuit board 54 in surrounding relation to an opening 69 for receiving the snap contact 63 of electrode 60. After the spring contact 58 has been positioned in the recess 66a to provide the desired spring contact, the legs 67 are inserted into holes 68 and the coupling loop 64 is inserted into opening 65. This prevents relative movement between the spring contact 58 and the mounting member 59. In addition, a small pair of legs 65a are provided in the recess 65 and straddle the legs 61 to impede the spread of the free end of legs 61. This adapts the apparent resiliency and thus the engagement force of the shape of contact 63.

Figure 4:
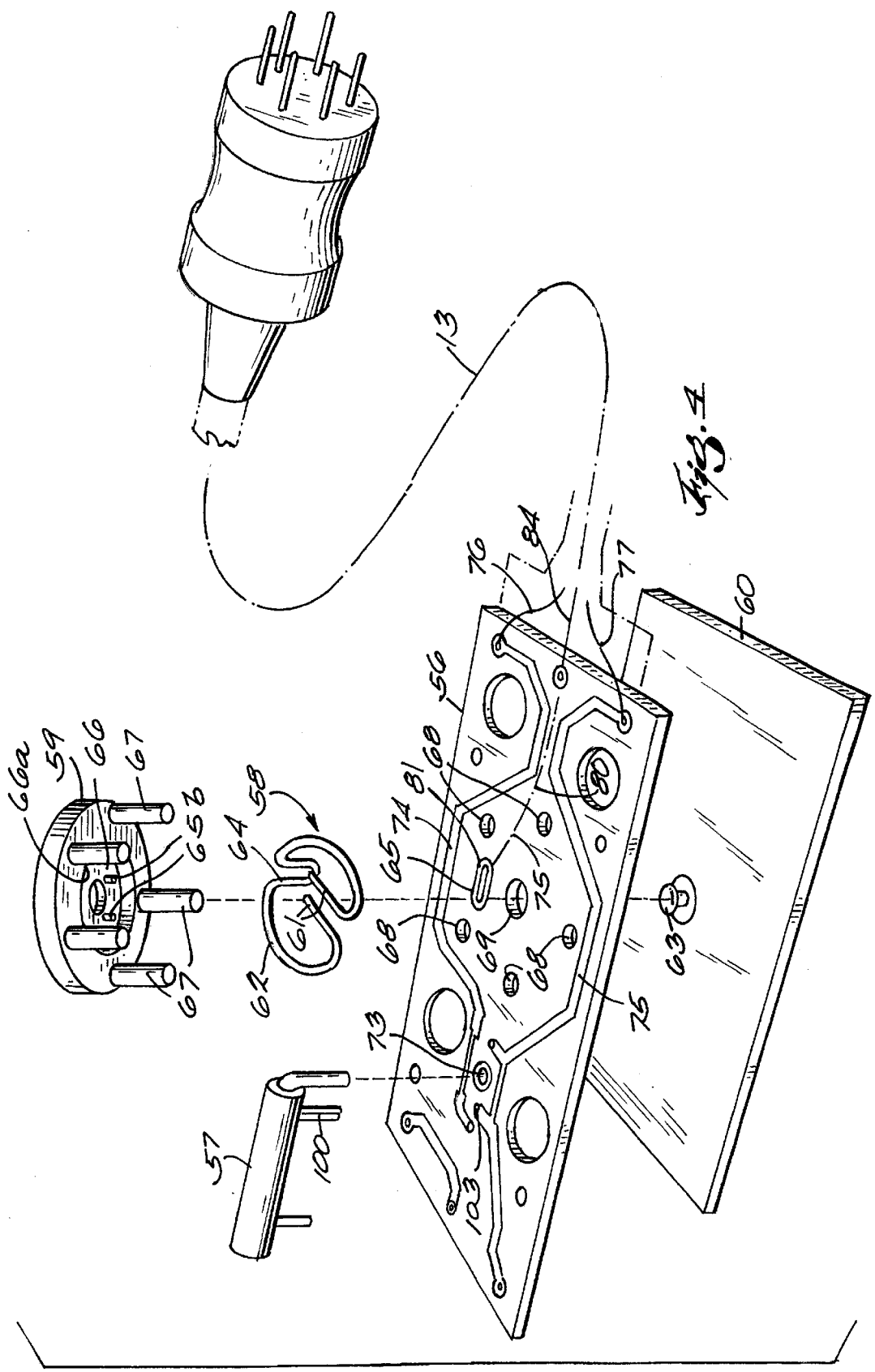
FIG. 4 is an exploded perspective view of the fetal monitoring coupling assembly used with the connector assembly shown in FIG. 1.
Figure 5:
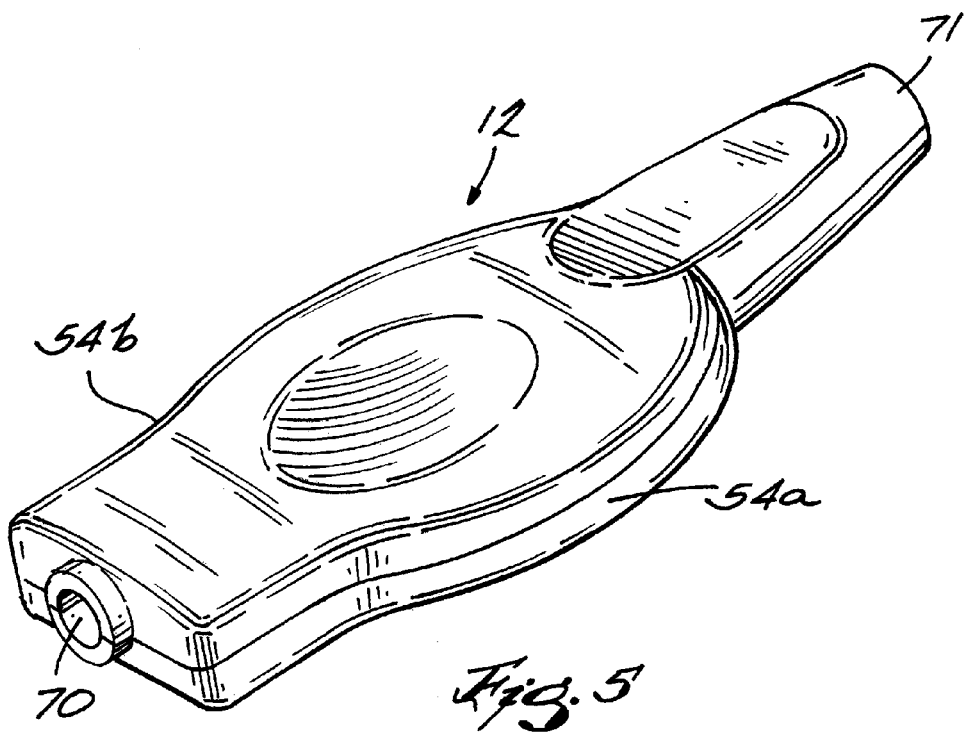
FIGS. 5 and 6 are top and bottom perspective views, respectively, of the coupling assembly of FIG. 4.
Figure 6:
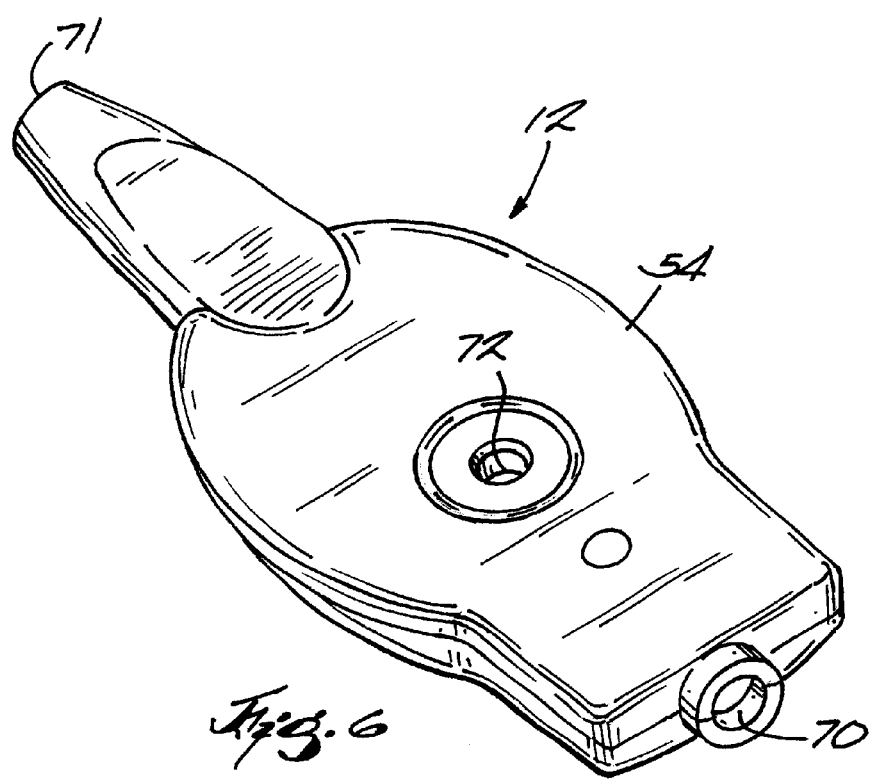

While the spring 58 and the mounting member 59 are shown in FIG. 4 above the circuit board 56, in actual practice, it may be disposed above or below the circuit board. In addition, while member 59 is shown to be a separate piece, it may be formed as an integral part of the upper or lower housing portions 54a or 54b.

The housing 54 is formed of any suitable moldable insulating material for encapsulating the circuit board 56, the plug 57, the spring contact 58 and the mounting member 59. A first opening 70 in the front of housing 54 communicates with the plug 57, a second opening 71 at the rear of the housing 54 receives cable 13, and a third opening 72 in the bottom of housing 54 communicates with the spring contact 58.

Circuit board 54 is formed of a suitable, semi-rigid, insulating material and includes an opening 73 adjacent its forward end for receiving the plug 57. Conductive strips 74 and 75 are provided on circuit board 54 and are, respectively, connected at one end to third and fourth contacts within the plug 57 and at their other ends do the conductors 76 and 77 which form a part of the cable 13. In addition, a conductive strip 80 on the opposite side of circuit board 57 is connected at one end to a snap contact 81 surrounding opening 65 for engagement with spring contact 58. The other end of strip 80 is connected to conductor 84 which also forms a part of the cable 13.

Figure 7:
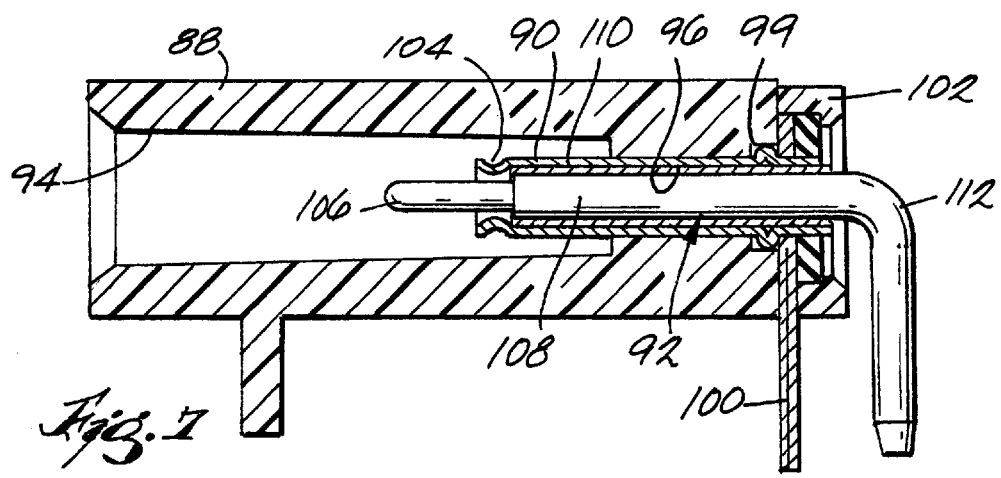
FIG. 7 is a cross-sectional view of a plug connector which forms a portion of the assembly of FIG. 1.

The plug 57 is shown more particularly in FIG. 7 to include an outer tubular shell 88, a first coaxial contact 90 and a second coaxial contact 92. The outer shell 88 has a cylindrical central bore 94 sized for receiving the sheath 41 of connector 28 with a sliding fit. The first contact 90 consists of a generally tubular conductive member which is received in a counter bore 96 in the end of shell 88. A bead 98 is formed adjacent the fixed end of contact 90 for engaging a complimentary hole formed in an elongate, downwardly extending conductive member 100 that is held in position by an end cap 102. Conductive member 100 is received in an opening 103 in circuit board 56 and is electrically connected to conductive strip 75.

The outer diameter of the free end of contact 90 is sized to receive the inner surface 39 of the forward contact 30 of connector 28. A groove 104 is formed in the forward end of contact 90 and that portion of the contact is unsupported to permit the contact to flex for receiving the detents 38 formed on the contact 30.

The second contact 92 comprises a rod-like member formed of a suitable conducting material. The forward end 106 of contact 92 has a diameter sized to telescopingly receive the contact 32. A larger diameter portion 108 of contact 92 is received within the tubular contact 90 and is separated therefrom by a sleeve of electrically insulating material 110. The portion 108 extends through an opening 112 formed in the end cap 102 and downwardly therefrom into opening 73 in the circuit board 56 and is electrically connective to the conductive strip 74.

Figure 9:
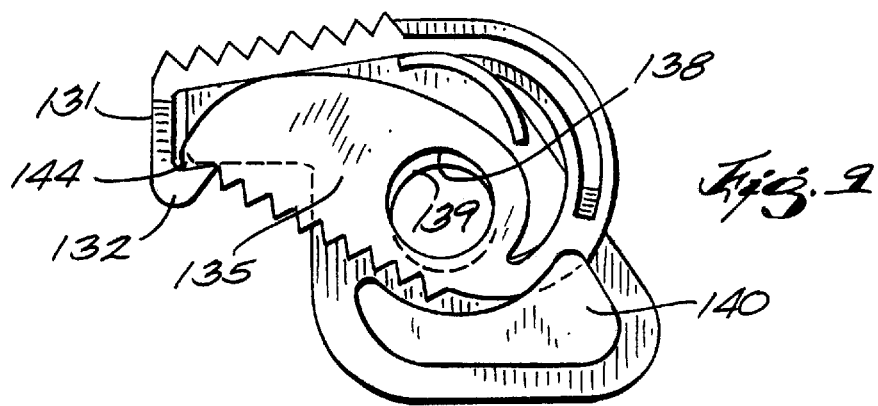
FIGS. 9 and 10 show the latch of FIG. 7 in its latching and unlatching modes.
Figure 10:
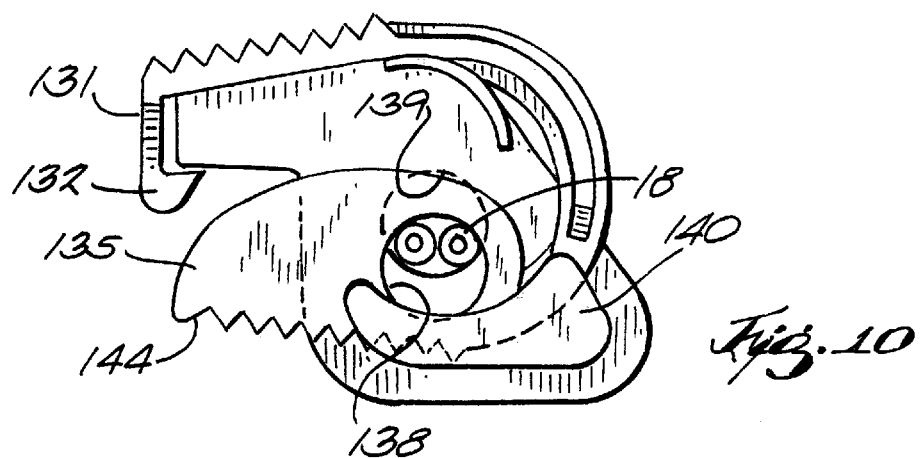
Figure 8:
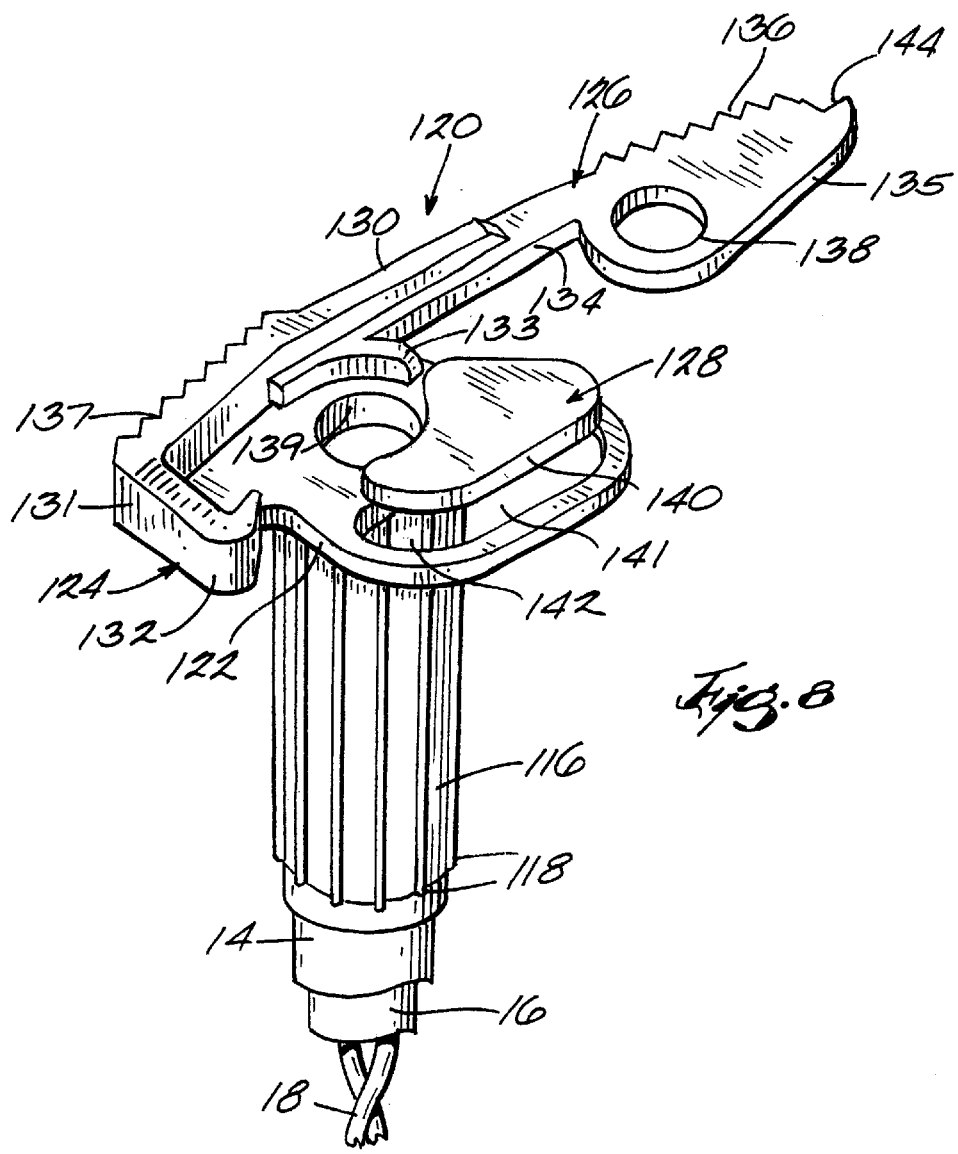
FIG. 8 is a perspective view of a clamp which forms a portion of the assembly of FIG. 1.

The clamp 25 is preferably formed of a plastic material and is shown in FIG. 8 in its free molded form and in FIGS. 9 and 10 in its operative mode as will be described more fully below. Clamp 25 includes a hollow tubular neck portion 116 which is fixed at one end to the drive tube 16 and a clamping portion 120 fixed to the opposite end of neck portion 116. The outer surface of the neck portion 116 may have a plurality of longitudinal flutes 118 to facilitate gripping.

The clamping portion 120 includes a planer base 122, a front latch 124, a clamp 126 and a retainer 128. A side wall 130 is formed along one side of the base 122 and extends upwardly therefrom. Latch 124 includes an arm 131 attached at one end to the forward end of sidewall 130 and in parallel with the front of the base 122. A hook 132 is formed at the free end of arm 131. At the rear of the base 122 and between the side wall 130 and the retainer 128 is an arcuate nesting wall 133.

The clamp 126 includes an arm 134 extending rearwardly from the side wall 130 and a clamp member 135 formed at the free end of arm 134. The outer side of the clamp member 135 is serrated at 136 to form a non-slip finger engaging surface. The outer surface of the side wall 130 is also serrated at 137 for the same purpose. It is important to note that the serrations at 136 and 137 are not necessary. A hole 138 is formed in the clamp member 135 for receiving the twisted pair 18 as will be discussed more fully below. There is also a similarly sized hole 139 in the base 122 which communicates with the interior of the neck portion 116 and the drive tube 16.

The retainer 128 includes an upper plate 140 supported by a side wall 141 in a parallel spaced apart relation above the base 122. The forward end of the plate 140 extends beyond that of the wall 141 to define a gap 142.

In operation, the arm 134 is bent inwardly and flexed slightly upwardly to permit the clamp member 135 to pass around the inner edge of the plate 140 and down into the space between the plate 140 and the base 122 as the arm 134 flexes about the nesting wall 133. As the clamp member 135 moves inwardly, it engages the hook 132. This causes the arm 131 to flex outwardly until a catch 144 on clamp 135 is positioned as shown in FIG. 9, after which the arm 130 returns to its position shown in FIG. 9 to latch the clamp member 135 in this position. The twisted pair 18 may then be inserted into the drive tube 116 through holes 138 and 139 after which the clamping member 135 is released from hook 132. This clamps the twisted pair 18 between the edges of the holes 138 and 139 and against movement relative to the drive tube 16 as shown in FIG. 10.

After the twisted pair 18 has been secured, the fetal electrode 20 is positioned in the mother as discussed in U.S. Pat. No. Re 28,990, after which the guide tube 16 and the guide tube 14 are removed. The connector 28 is then inserted into the coaxial plug 57 and the snap spring contact 58 is coupled to the electrode 60 which may then be attached to the mother's leg. Because the contacts 30 and 32 of connector 28 and 90 and 92 of plug 57 are circular in cross section, the connection can be made without the necessity of orienting the connector 28.

Figure 11:
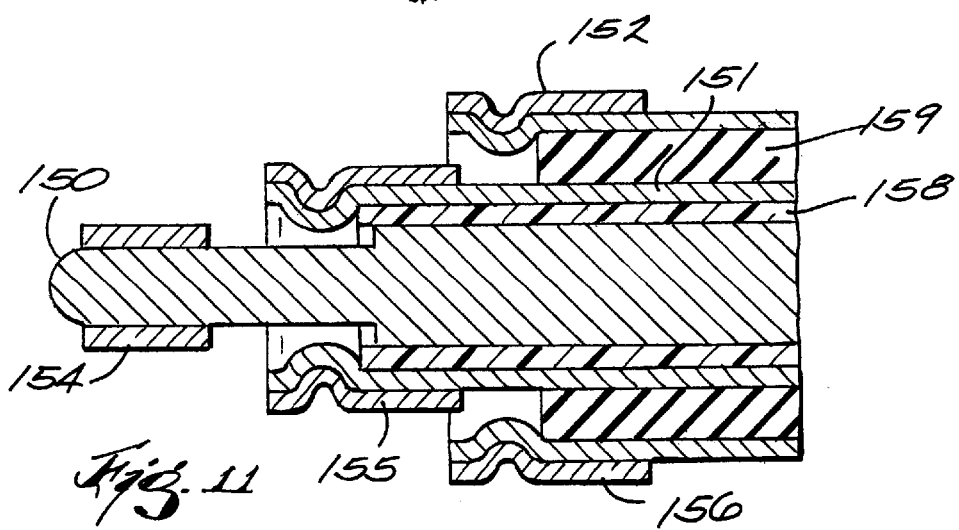
FIG. 11 shows another embodiment of the invention.

While a bipolar connector is shown in FIGS. 3 and 7, the connector and plug may include three or more conductive paths as shown in FIG. 11. Here, the plug includes first, second and third coaxial contacts 150, 151, and 152 and the connector includes cylindrical, coaxial, axially spaced contacts 154, 155 and 156. Insulating sleeves 158 and 159 electrically isolate contacts 150, 151 and 152.

FIGS. 12–15 illustrate yet another embodiment of a connector assembly for a fetal scalp electrode. Like parts have been given like reference numerals. As seen in FIGS. 12 and 15, the fetal scalp electrode assembly includes a connector 228 attached to the proximal end of the twisted pair 18 in accordance with the invention. The connector 228 includes a generally cylindrical contact 230 and a pin contact 232 coaxial with the cylindrical contact 230. The contacts 230 and 232 are formed of a suitable conductive material, such as copper, brass or nickel. The cylindrical contact 230 is coupled at the rear to the conductor 18a of the twisted pair 18 and includes an inner surface 235 and an elongated slit 237. The pin contact 232 is coupled at the rear to the conductor 18b of the twisted pair 18. The conductors 18a and 18b, and the respective contacts 230 and 232, are connected in a suitable manner, such as by welding or soldering, but may also be connected in other ways (not shown) such as by pinch or press-fit contact, or any other method of mechanically securing two electrical conductors together to provide a low impedance connection. A shell or sheath 241 is fixed in a surrounding relation to the contacts 230 and 232 and is overmolded to bond to the twisted pair 18. The inner surface 244 of the sheath 241 engages the outer surface 246 of the cylindrical contact 230 and a portion of the outer surface 248 of the pin contact 232. The forward end of the sheath 241 extends beyond the forward ends of the contacts 230 and 232.

Still referring to FIGS. 12–15, the fetal scalp electrode assembly also includes a plug or coupling device 257 including an outer tubular shell 288. Mounted in the tubular shell 288 are a center conductor 290, and an outer conductor 294 coaxially mounted on the center conductor 290 and electrically isolated from the center conductor 290 by a sleeve of electrically insulating material 298. The outer shell 288 has a cylindrical central bore 302 sized for receiving one end of the sheath 241 of the connector 228 with a slight clearance fit. The center conductor 290 is generally cylindrical and has (see FIG. 14) an axial opening 306 in the proximal end, making at least a portion of the center conductor 290 tubular. An internal spring contact 310 (see FIGS. 13–15) is disposed inside the tubular portion of the center conductor 290 and is in electrical contact therewith. The internal spring contact 310 has a central bore 314 and resilient contact fingers 318 spaced radially around the distal end of the bore 314. As best seen in FIG. 13, the resilient contact fingers 318 are biased radially inward (shown in solid in FIG. 13) toward the bore 314 and are outwardly deflectable away from the bore 314 (shown in phantom in FIG. 13). It is important to note that the internal spring contact 310 need not be a separate part, but rather could be integrally formed with the center conductor 290. The center conductor 290 and internal spring contact 310 are made of a suitable conductive material and are electrically connected to the circuit board 56 via terminal 322 adjacent the rear of the tubular shell 288. The terminal 322 is connected to the circuit board 56 in a similar manner to that shown in FIG. 4. The terminal 322 extends downwardly into opening 73 and is electrically connected to conductive strip 74 on the circuit board 56.

The outer conductor 294 is substantially cylindrical and is mounted on the sleeve of insulating material 298. The outer conductor is made from a suitable conductive material and includes a hollow body portion 326, a rearwardly extending flange 330 connected to a terminal 334, and two rearwardly extending resilient spring contact fingers 338. Other embodiments (not shown) may have only one spring contact finger 338, or alternatively, may have more than two. The hollow body portion 326 includes a slot or opening 340 extending the length of the hollow body portion 326. The slot 340 permits the body portion 326 to flex when slid over the end of the center conductor 290 during assembly. Each spring contact finger 338 is biased radially outward toward the shell 288 and includes at least one outwardly protruding dimple 342 extending from the outer surface 346. The terminal 334 is connected to the circuit board 56 in a similar manner to that shown in FIG. 4. The terminal 334 extends downwardly into opening 103 in the circuit board 56 and is electrically connected to the conductive strip 75.

As the connector 228 is inserted into the coupling device 257, the cylindrical contact 230 slides over the center conductor 290, insulating sleeve 298 and body portion 326. As the cylindrical contact 230 slides over the resilient spring contact fingers 338, the inner surface 235 causes the resilient spring contact fingers 338 to deflect radially inward until the dimples 342 engage the inner surface 235. The radially outward bias of the resilient contact fingers 338 maintains a stable electrical contact between the dimples 342 and the inner surface 235. At the same time, the pin contact 232 is being inserted into the bore 314 of the internal spring contact 310. As the pin contact 232 extends through the bore 314, the resilient contact fingers 318 engage the outer surface 248 and deflect radially outward. The radially inward bias of the contact fingers 318 maintains a stable electrical contact between the contact fingers 318 and the outer surface 248.

Other features and advantages of the invention are set forth in the following claims.

What is claimed is:

1. An apparatus comprising:
    a fetal scalp electrode assembly including a holder formed of an insulating material, a fetal electrode and a maternal electrode secured to the holder, an insulated pair of elongated flexible wires, each of the wires electrically connected to a respective one of the fetal and maternal electrodes, and a connector having a pin contact electrically connected to a one of the wires and a cylindrcal contact electrically connected to the other of the wires and mounted coaxially with the pin contact so that the contacts are electrically isolated from each other; and
    a coupling device including a housing defining a cavity having an opening for receiving the connector, a center conductor mounted in the cavity and including a tubular portion substantially coaxial with and spaced from the opening, and an outer conductor mounted in the cavity and including a tubular portion coaxial with and electrically isolated from the center conductor;
    wherein the outer conductor further includes a resilient spring contact finger extending from the tubular portion and away from the opening.

2. The apparatus set forth in claim 1, wherein the cylindrical contact is spaced axially from the pin contact.

3. The apparatus set forth in claim 1, further comprising an elongated tubular sheath covering the connector and sized to be received in the coupling device, the sheath having a first end extending over and receiving ends of the pair of flexible wires, and a second end being open and spaced from each of the contacts so that a gap is formed between the contacts and the second end of the sheath.

4. The apparatus set forth in claim 3, wherein each of the contacts has a forward end and a rear end, wherein the wires are connected respectively to the rear ends of the contacts, and wherein the second end of the sheath extends beyond the forward ends of the contacts.

5. The apparatus set forth in claim 4, wherein the cylindrical contact is adjacent the second end of the sheath and the pin contact is adjacent the first end of the sheath such that the rear end of the cylindrical contact is spaced from the forward end of the pin contact.

6. The apparatus set forth in claim 1, wherein the resilient spring contact finger is biased outwardly.

7. The apparatus set forth in claim 1, wherein the resilient spring contact finger includes a dimple.

8. The apparatus set forth in claim 1, wherein the outer conductor further includes two resilient spring contact fingers extending from the tubular portion and away from the opening.

9. The apparatus set forth in claim 1, further including a tubular member disposed within the housing and having one end communicating with the opening, the center conductor and outer conductor being disposed within the tubular member.

10. An apparatus comprising:
    a fetal scalp electrode assembly including a holder formed of an insulating material, a fetal electrode and a maternal electrode secured to the holder, an insulated pair of elongated flexible wires, each of the wires electrically connected to a respective one of the fetal and maternal electrodes, and a connector having a pin contact electrically connected to a one of the wires and a cylindrical contact electrically connected to the other of the wires and mounted coaxially with the pin contact so that the contacts are electrically isolated from each other; and
    a coupling device including a housing defining a cavity having an opening for receiving the connector, a center conductor mounted in the cavity and including a tubular portion substantially coaxial with and spaced from the opening, and an outer conductor mounted in the cavity and including a tubular portion coaxial with and electrically isolated from the center conductor;
    wherein the center conductor further includes an internal spring contact inside the tubular portion and wherein the internal spring contact includes a resilient spring contact finger extending away from the opening.

11. The apparatus set forth in claim 10, wherein the cylindrical contact is spaced axially from the pin contact.

12. The apparatus set forth in claim 10, wherein the fetal scalp electrode assembly further includes an elongated tubular sheath covering the connector and sized to be received in the opening of the coupling device, the sheath having a first end extending over and receiving ends of the pair of flexible wires, and a second end being open and spaced from each of the contacts so that a gap is formed between the contacts and the second end of the sheath.

13. The apparatus set forth in claim 12, wherein each of the contacts has a forward end and a rear end, wherein the wires are connected respectively to the rear ends of the contacts, and wherein the second end of the sheath extends beyond the forward ends of the contacts.

14. The apparatus set forth in claim 13, wherein the cylindrical contact is adjacent the second end of the sheath and the pin contact is adjacent the first end of the sheath such that the rear end of the cylindrical contact is spaced from the forward end of the pin contact.

15. The apparatus set forth in claim 10, further including a tubular member disposed within the housing and having one end communicating with the opening, the center conductor and outer conductor being disposed within the tubular member.

16. The apparatus set forth in claim 10, wherein the resilient spring contact finger is biased inwardly.

17. The apparatus set forth in claim 10, wherein the internal spring contact includes two resilient spring contact fingers extending away from the opening.

18. An apparatus comprising:

a fetal scalp electrode assembly including a holder formed of an insulating material, a fetal electrode and a maternal electrode secured to the holder, an insulated pair of elongated flexible wires, each of the wires electrically connected to a respective one of the fetal and maternal electrodes, a connector having a pin contact electrically connected to a one of the wires and a cylindrical contact electrically connected to the other of the wires, the cylindrical contact being axially spaced from the pin contact and mounted coaxially with the pin contact so that the contacts are electrically isolated from each other, and an elongated tubular sheath covering the connector, the sheath having a first end extending over and receiving ends of the pair of flexible wires, and a second end being open and spaced from each of the contacts so that a gap is formed between the contacts and the second end of the sheath; and a coupling device including a housing defining a cavity having an opening for receiving the sheath, a center conductor mounted in the cavity and including a tubular portion substantially coaxial with and spaced from the opening, an internal spring contact inside the tubular portion of the center conductor, the internal spring contact including an inwardly biased resilient spring contact finger extending away from the opening, and an outer conductor mounted in the cavity and including a tubular portion coaxial with and electrically isolated from the center conductor and an outwardly biased resilient spring contact finger extending from the tubular portion and away from the opening.

* * * * *